United States Patent
Kobayashi et al.

(10) Patent No.: US 8,466,303 B2
(45) Date of Patent: Jun. 18, 2013

(54) PROCESS FOR PRODUCTION OF EPOXY COMPOUND

(75) Inventors: Yuji Kobayashi, Minato-ku (JP); Hiroshi Uchida, Minato-ku (JP); Kazuhiko Sato, Tsukuba (JP); Yoshihiro Kon, Tsukuba (JP)

(73) Assignees: Showa Denko K.K., Tokyo (JP); National Institute of Advanced Industrial Science and Technology, Tokyo (JP)

( * ) Notice: Subject to any disclaimer, the term of this patent is extended or adjusted under 35 U.S.C. 154(b) by 245 days.

(21) Appl. No.: 12/920,097

(22) PCT Filed: Feb. 20, 2009

(86) PCT No.: PCT/JP2009/053611
§ 371 (c)(1),
(2), (4) Date: Aug. 27, 2010

(87) PCT Pub. No.: WO2009/107754
PCT Pub. Date: Sep. 3, 2009

(65) Prior Publication Data
US 2011/0009652 A1   Jan. 13, 2011

(30) Foreign Application Priority Data
Feb. 28, 2008  (JP) ................................. 2008-048101

(51) Int. Cl.
*C07D 301/12*  (2006.01)
(52) U.S. Cl.
USPC ........................................ 549/531; 549/533
(58) Field of Classification Search
USPC .................................. 549/531, 533
See application file for complete search history.

(56) References Cited

FOREIGN PATENT DOCUMENTS

| | | |
|---|---|---|
| EP | 1 473 290 A1 | 11/2004 |
| EP | 1 618 953 A1 | 1/2006 |
| JP | 04-283542 A | 10/1992 |
| JP | 08-027136   * | 1/1996 |
| JP | 08-027136 A | 1/1996 |
| JP | 2006-316034  * | 11/1996 |
| JP | 09-003005 A | 1/1997 |
| JP | 11-349579    * | 12/1999 |
| JP | 11-349579 A | 12/1999 |
| JP | 2006-316034 A | 11/2006 |
| WO | 2006/123814 A2 | 11/2006 |

OTHER PUBLICATIONS

Teshigahara et al, Synthesis of Alicyclic Epoxy (meth)acrylates, Toso Kenkyu,Hokoku, 1991, 35(02), p. 47-56,(abstract page ).*
Yasutaka Ishii, et al., "Hydrogen Peroxide Oxidation Catalyzed by Heteropoly Acids Combined with Cetylpyridinium Chloride: Epoxidation of Olefins and Allylic Alcohols, Ketonization of Alcohols and Diols, and Oxidative Cleavage of 1,2-Diols and Olefins," J. Org. Chem., 1988, pp. 3587-3593, vol. 53, No. 15.
Michiel C. A. Van Vliet, et al., "Perfluoroheptadecan-9-one: a selective and reusable catalyst for epoxidations with hydrogen peroxide," Chem. Commun. 1999, pp. 263-264.
Supplementary European Search Report issued in corresponding European Application No. 09 71 5158, on Jun. 27, 2011.

* cited by examiner

*Primary Examiner* — Taylor Victor Oh
(74) *Attorney, Agent, or Firm* — Sughrue Mion, PLLC

(57) ABSTRACT

A novel process for producing a polyfunctional epoxy monomer is provided that facilitates separation of an aqueous layer catalyst from a reaction solution and has satisfactory hydrogen peroxide efficiency by reacting an aqueous hydrogen peroxide solution with a polyolefin without using an organic solvent and under mild conditions. The process in the present invention is a process for producing a corresponding epoxy compound by reacting an organic compound having a carbon-carbon double bond with hydrogen peroxide present in an aqueous hydrogen peroxide solution to epoxidate the double bond, wherein a tungsten compound and tertiary amine are used as reaction catalysts.

9 Claims, No Drawings

PROCESS FOR PRODUCTION OF EPOXY COMPOUND

TECHNICAL FIELD

The present invention relates to a process for producing an epoxy compound, which comprises the step for converting a carbon-carbon double bond of an organic compound to an epoxy group without using an organic solvent as a reaction solvent and by using a highly active catalyst system. More particularly, the present invention relates to a process for epoxidating a diolefin so as to obtain an organic polyfunctional epoxy monomer in which an epoxy group and double bond are contained in a molecule thereof.

BACKGROUND ART

Organic polyfunctional epoxy monomers are useful compounds that can be widely used in various industrial fields including the chemical industry as raw materials of resist materials (and particularly solder resist materials), and as intermediates of agricultural chemicals and pharmaceuticals as well as raw materials of various polymers such as plasticizers, adhesives or coating resins.

However, technology for selectively epoxidating only one double bond at a specific position in a diolefin has low productivity (low reactivity, low selectivity), and the technical scope of that technology is frequently limited to only certain types of structures.

Although peracids have conventionally been used as selective epoxidation agents for diolefins (see, for example, Chem. Ber., 1985, 118, 1267-1270), this technique has problems such as the formation of large amounts of diepoxides as by-products and corrosion of equipment due to the equivalent formation of acid derived from an oxidizing agent.

Although a process for selectively epoxidating diolefins is also known that uses oxone as an oxidizing agent in the presence of a ketone catalyst (see, for example, J. Org. Chem., 1998, 63, 2948-2953), in this reaction, in addition to requiring a considerably large amount of the ketone catalyst (20 to 30 mol % based on the diolefin), there is also the problem of the need to rigorously control reaction conditions such as the pH of the reaction solution and reaction temperature in order to inhibit decomposition of oxone during the reaction.

On the other hand, hydrogen peroxide is an oxidizing agent that is excellent for industrial use since it is inexpensive, does not cause corrosion, and places little burden on the environment since it does not form any by-products after reacting or only forms water.

Examples of conventional known processes for producing epoxy compounds from olefins using hydrogen peroxide as an epoxidation agent include: (1) an epoxidation process that uses hydrogen peroxide in the presence of quaternary ammonium chloride, phosphoric acid and a tungsten metal salt (see Japanese Unexamined Patent Publication No. 2003-192679 (hereinafter referred to as Patent Document 1) and Japanese Unexamined Patent Publication No. 2004-115455 (hereinafter referred to as Patent Document 2)), (2) an epoxidation process that uses a phase transfer catalyst in the manner of a quaternary ammonium salt and uses a tungstic acid and an α-aminomethylphosphonic acid as catalysts in an organic solvent (see Japanese Unexamined Patent Publication No. H8-27136 (hereinafter referred to as Patent Document 3)), (3) an epoxidation process carried out in the presence of a tungsten oxide obtained by reacting a tungsten compound and hydrogen peroxide, quaternary ammonium hydrogen sulfate and phosphoric acid in a toluene solvent (see Japanese Unexamined Patent Publication No. 2004-59573 (hereinafter referred to as Patent Document 4)), (4) an epoxidation process that uses a multi-component oxidation catalyst comprising a tungsten compound, quaternary ammonium salt, phosphoric acid and/or boric acid and hydrogen sulfate in the presence of an organic solvent such as toluene (see Japanese Unexamined Patent Publication No. 2005-169363 (hereinafter referred to as Patent Document 5), and (5) an epoxidation process carried out in a chloroform solvent using a catalyst having both phase transfer ability and epoxidation ability such as a cetylpyridinium salt of a heteropolyacid (see J. Org. Chem., 1988, 53, 3587-3593 (hereinafter referred to as Non-Patent Document 1)). However, since all of these processes use an organic solvent and a quaternary ammonium salt having both phase transfer ability and high surface activation ability, reaction efficiency as well as ease of separation of the organic layer and aqueous layer following reaction are not satisfactory.

In addition, although a reaction system has also been reported in which a reaction is carried out without using an organic solvent (see Japanese Unexamined Patent Publication No. 2006-316034 (hereinafter referred to as Patent Document 6)), in this system as well, since it is necessary to use a catalyst having strong phase transfer ability in the manner of a quaternary ammonium salt, and since the phase transfer catalyst has surface activity, phase separation following completion of the reaction is not easy.

In addition, not only is phase separation not easy, but when a quaternary ammonium salt is mixed into the organic layer an attempted to be used, it has serious detrimental effects on electrical properties and the like, and in the case of carrying out distillation or other purification, the quaternary ammonium salt is decomposed by heat, thereby resulting in problems such as poor distillation yield.

Known examples of processes that use a catalyst other than tungsten include: (6) an epoxidation process that uses hydrogen peroxide and a catalyst in which methyl trioxolenium ($CH_3ReO_3$) and a strong organic base compound are loaded on an inorganic oxide support (see Japanese Unexamined Patent Publication No. 2001-25665 (hereinafter referred to as Patent Document 7)), (7) an epoxidation process that uses hydrogen peroxide in the presence of a titanium-containing zeolite catalyst and an additive containing a tertiary amine, tertiary amine oxide or mixture thereof (see Japanese Unexamined International Patent Publication No. 2002-526483 (hereinafter referred to as Patent Document 8), and (8) an epoxidation process that uses hydrogen peroxide in the presence of a fluoroalkylketone (see Chem. Commun., 1999, 263-264 (hereinafter referred to as Non-Patent Document 2)). However, these processes have poor catalytic efficiency, require an excess of hydrogen peroxide, or are subject to restrictions such as only being able to be applied to small substrates.

PRIOR ART PUBLICATIONS

Patent Documents

Patent Document 1: Japanese Unexamined Patent Publication No. 2003-192679
Patent Document 2: Japanese Unexamined Patent Publication No. 2004-115455
Patent Document 3: Japanese Unexamined Patent Publication No. H8-27136
Patent Document 4: Japanese Unexamined Patent Publication No. 2004-59573

Patent Document 5: Japanese Unexamined Patent Publication No. 2005-169363
Patent Document 6: Japanese Unexamined Patent Publication No. 2006-316034
Patent Document 7: Japanese Unexamined Patent Publication No. 2001-25665
Patent Document 8: Japanese Unexamined International Patent Publication No. 2002-526483

Non-Patent Documents

Non-Patent Document 1: J. Org. Chem., 1988, 53, 3587-3593
Non-Patent Document 2: Chem. Commun., 1999, 263-264

DISCLOSURE OF THE INVENTION

Problems to be Solved by the Invention

Thus, since there is a strong desire to develop a process for selectively producing a bifunctional epoxy monomer from a diolefin at satisfactory yield and low cost and by using a simple and safe procedure without the use of an organic solvent and under mild conditions, an object of the present invention is to provide a novel process for producing a polyfunctional epoxy monomer that facilitates separation of an aqueous layer catalyst from the reaction solution and has satisfactory hydrogen peroxide efficiency by reacting an aqueous solution of hydrogen peroxide with a compound having a plurality of carbon-carbon double bonds in a molecule thereof without using an organic solvent and under mild conditions.

Means for Solving the Problems

As a result of repeatedly conducting extensive research and experiments to solve the aforementioned problems, the inventors of the present invention recently surprisingly found that by reacting hydrogen peroxide with an olefin by using a tungsten compound and tertiary organic amine as catalysts without using an organic solvent and without using a strong phase transfer catalyst in the manner of a quaternary ammonium salt, a corresponding epoxy compound is selectively formed at high yield, thereby leading to completion of the present invention.

More specifically, the present invention comprises the following [1] to [12]:

[1] a process for producing an epoxy compound, comprising: producing a corresponding epoxy compound by reacting an organic compound having a carbon-carbon double bond with hydrogen peroxide present in an aqueous hydrogen peroxide solution to epoxidate the double bond; wherein a tungsten compound and a tertiary amine are used as reaction catalysts;

[2] a process for producing an epoxy compound, comprising: producing a corresponding epoxy compound by reacting an organic compound having a carbon-carbon double bond with hydrogen peroxide present in an aqueous hydrogen peroxide solution to epoxidate the double bond; wherein an organic solvent is not used as a reaction solvent, and a tungsten compound and tertiary amine are used as reaction catalysts;

[3] the process for producing an epoxy compound according to [1] or [2] above, wherein a mineral acid and/or partially neutralized salt thereof is further used as a co-catalyst;

[4] the process for producing an epoxy compound according to any one of [1] to [3] above, wherein an α-aminomethylphosphonic acid compound represented by the following structural formula:

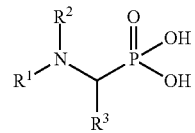

(wherein $R^1$ represents a hydrogen atom or acyl group, and $R^2$ and $R^3$ each independently of the other represent a hydrogen atom or $C_1$-$C_{18}$ alkyl group or $C_1$-$C_{18}$ aryl) is further used as a co-catalyst;

[5] the process for producing an epoxy compound according to any one of [1] to [4] above, wherein the organic compound having a carbon-carbon double bond is a compound represented by the following formula:

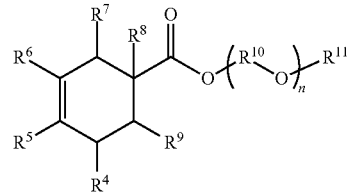

(wherein $R^4$, $R^5$, $R^6$, $R^7$ and $R^8$ each independently of the other represent a hydrogen atom or methyl group, $R^9$ represents a hydrogen atom, methyl group, phenyl group or the following $R^{12}$:

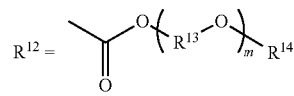

(wherein $R^{13}$ represents an $C_2$-$C_8$ alkylene or $C_2$-$C_8$ cycloalkylene group, $R^{14}$ represents an $C_1$-$C_{10}$ alkyl group, $C_1$-$C_{10}$ cycloalkyl group, $C_1$-$C_{10}$ aryl group, $C_1$-$C_{10}$ alkenyl group or $C_1$-$C_{10}$ cycloalkenyl group, and m represents an integer of 0 to 5), $R^{10}$ represents an $C_2$-$C_8$ alkylene or $C_2$-$C_8$ cycloalkylene group, $R^{11}$ represents an $C_1$-$C_{10}$ alkyl group, $C_1$-$C_{10}$ cycloalkyl group, $C_1$-$C_{10}$ aryl group, $C_1$-$C_{10}$ alkenyl group or $C_1$-$C_{10}$ cycloalkenyl group, and n represents an integer of 0 to 5);

[6] the process for producing an epoxy compound according to any one of [1] to [5] above, wherein the compound having a carbon-carbon double bond has a plurality of carbon-carbon double bonds, and only one of the plurality of carbon-carbon double bonds is selectively epoxidated;

[7] the process for producing an epoxy compound according to [6] above, wherein the organic compound having a plurality of carbon-carbon double bonds is a compound composed of a combination of a cyclohexene derivative and a terminal vinyl or vinylidene group, and the carbon-carbon double bond moiety of the cyclohexene derivative is epoxidated;

[8] the process for producing an epoxy compound according to [6] or [7] above, wherein the organic compound having a plurality of carbon-carbon double bonds is a compound represented by the following formula:

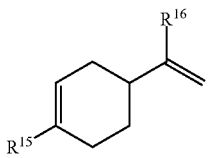

(wherein, $R^{15}$ and $R^{16}$ represent hydrogen atoms or methyl groups);

[9] the process for producing an epoxy compound according to [6] or [7] above, wherein the organic compound having a plurality of carbon-carbon double bonds is a compound represented by the following formula:

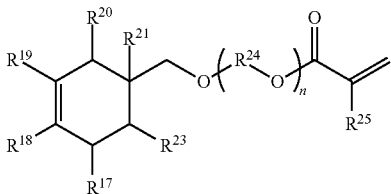

(wherein, $R^{17}$, $R^{18}$, $R^{19}$, $R^{20}$, $R^{21}$, and $R^{25}$ independently of the other represent a hydrogen atom or methyl group, $R^{23}$ represents a hydrogen atom, methyl group or phenyl group, $R^{24}$ represents an $C_2$-$C_8$ alkylene or $C_2$-$C_8$ cycloalkylene group, and n represents an integer of 0 to 5);

[10] the process for producing an epoxy compound according to any one of [1] to [9] above, wherein the tungsten compound is sodium tungstate, and the tertiary amine is a tertiary amine having an alkyl group in which the total number of carbon atoms is 6 or more;

[11] the process for producing an epoxy compound according to any one of [3] to [10] above, wherein the mineral acid and/or partially neutralized salt thereof is at least one type selected from the group consisting of phosphoric acid, sulfuric acid and boric acid and/or partially neutralized salts thereof;

[12] the process for producing an epoxy compound according to any one of [1] to [11] above, wherein the total number of carbon atoms of an alkyl group of the tertiary amine is 12 to 40; and,

[13] the process for producing an epoxy compound according to [6] above, wherein the organic compound having a plurality of carbon-carbon double bonds is 3-cyclohexenylmethyl (meth)acrylate and/or allyl 3-cyclohexene-1-carboxylate.

Effects of the Invention

According to the process of the present invention, since an organic solvent is not used as a reaction solvent and it is not necessary to use a strong phase transfer catalyst in the manner of a quaternary ammonium salt, an aqueous layer containing a catalyst component and an organic layer containing a reaction substrate can be easily separated following the reaction. Moreover, an organic polyfunctional epoxy monomer, which is a useful substance that is widely used in various industrial fields including the chemical industry as raw materials of resist materials (and particularly solder resist materials), and as intermediates of agricultural chemicals and pharmaceuticals as well as raw materials of various polymers such as plasticizers, adhesives or coating resins, can be produced safely, at satisfactory yield and at low cost while using a simple procedure from a polyolefin involved in the reaction and an aqueous hydrogen peroxide solution. Thus, the process as claimed in the present invention yields considerable industrial effects. In addition, the process as claimed in the present invention also has the effect of reducing the burden on the environment since it does not use an organic solvent.

BEST MODE FOR CARRYING OUT THE INVENTION

Although there are no particular limitations on the concentration of the aqueous hydrogen peroxide used in the production process of the present invention, it is generally selected from the range of 1 to 80% and preferably 20 to 80%.

Although there are also no particular limitations on the amount of the aqueous hydrogen peroxide solution used, it is selected from the range of 0.8 to 10 equivalents, and preferably 1 to 3 equivalents, based on the olefin to be epoxidated.

Although naturally the concentration of the aqueous hydrogen peroxide is preferably high from the viewpoint of productivity, it goes without saying that it is preferable to not use an unnecessarily high concentration of aqueous hydrogen peroxide.

The tungstic acid compound used as a catalyst is a compound that forms tungstate anion in water, and although examples thereof include tungstic acid, tungsten trioxide, tungsten trisulfide, tungsten hexachloride, phosphotungstic acid, ammonium tungstate, potassium tungstate dihydrate and sodium tungstate dihydrate, tungstic acid, tungsten trioxide, phosphotungstic acid and sodium tungstate dihydrate are preferable. These tungsten compounds may be used alone or two more types may be used as a mixture. The amount of tungsten compound used is selected from the range of 0.0001 to 20 mol %, and preferably 0.01 to 20 mol %, based on the substrate olefin.

Although a tertiary amine in which the total number of carbon atoms of the organic alkyl group thereof is 6 or more and preferably 12 or more is used as a catalyst for the tertiary organic amine, that having a high degree of epoxidation reaction activity is preferable. Examples of such tertiary amines include tributylamine, tri-n-octylamine, tri-(2-ethylhexyl) amine, N,N-dimethyllaurylamine, N,N-dimethylmyristylamine, N,N-dimethylpalmitylamine, N,N-dimethylstearylamine, N,N-dimethylbehenylamine, N,N-dimethylcocoalkylamine, N,N-dimethyl tallow alkylamine, N,N-dimethyl hydrogenated tallow alkylamine, N,N-dimethyloleylamine, N,N-diisopropyl-2-ethylhexylamine, N,N-dibutyl-2-ethylhexylamine, N-methyldioctylamine, N-methyldidecylamine, N-methyldicocoalkylamine, N-methyl hydrogenated tallow alkylamine and N-methyldioleylamine. The total number of carbon atoms of the organic alkyl group may be 40 or less. These tertiary organic amines may be used alone or two or more types may be used as a mixture. The amount used is selected from the range of 0.0001 to 10 mol %, and preferably 0.01 to 10 mol %, based on the substrate olefin.

In addition, a mineral acid and/or partially neutralized salt thereof can be used as a co-catalyst. At least one type of mineral acid selected from the group consisting of phosphoric acid, sulfuric acid and boric acid and/or partially neutralized salts thereof can be used for the mineral acid. The amount of these mineral acids used is such that the molar ratio of protons of the mineral acid is selected from the range of 0.001 to 20 mol %, and preferably 0.1 to 20 mol %, based on 1 mole of double bonds of the substrate to be epoxidated. As an example thereof, in the case of using an olefin having two double bonds in a molecule thereof for the substrate olefin and using phosphoric acid for the mineral acid, the ratio at which both are used is such that the ratio of phosphoric acid used to the olefin having two double bonds in a molecule thereof is 0.01×⅔ to 20×⅔ mol % and preferably 0.1×⅔ to 20×⅔ mol % since phosphoric acid has three protons in a molecule thereof.

In addition, a partially neutralized salt of a mineral acid may be partially neutralized by a basic compound such as an alkaline metal, alkaline earth metal or organic amine. Among these mineral acids, phosphoric acid, sulfuric acid or the combined used of both is particularly preferable.

Moreover, the efficiency of the epoxidation reaction can be further enhanced by further using an α-aminomethylphosphonic acid compound represented by the following structural formula:

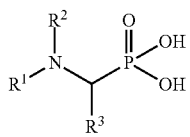

(wherein $R^1$ represents a hydrogen atom or acyl group, and $R^2$ and $R^3$ each independently of the other represent a hydrogen atom or $C_1$-$C_{18}$ alkyl group or $C_1$-$C_{18}$ aryl group) as a co-catalyst.

This α-aminomethylphosphonic acid can be synthesized using a process disclosed in, for example, Japanese Unexamined Patent Publication No. H5-112586. Examples of such α-aminomethylphosphonic acids include α-aminomethylphosphonic acid, α-aminoethylphosphonic acid, α-aminopropylphosphonic acid, α-aminobutylphosphonic acid, α-aminopentylphosphonic acid, α-aminohexylphosphonic acid, α-aminoheptylphosphonic acid, α-aminooctylphosphonic acid, α-aminononylphosphonic acid, α-amino-α-phenylmethylphosphonic acid, N-acetyl-α-aminomethylphosphonic acid, N-propionyl-α-aminomethylphosphonic acid, N-benzoyl-α-aminomethylphosphonic acid and N-(4-methoxybenzoyl)-α-aminomethylphosphonic acid. These α-aminomethylphosphonic acids may be used alone or two or more types may be used as a mixture. The amount used is selected from the range of 0.0001 to 5 mol %, and preferably 0.01 to 5 mol %, based on the substrate olefin.

In the process as claimed in the present invention, the reaction is normally carried out within a range of 30 to 120° C. and preferably within a range of 40 to 100° C.

In the process as claimed in the present invention, in the case of using an organic compound having a single carbon-carbon double bond, although that carbon-carbon double bond can be epoxidated, in the case of using an organic compound having a plurality of carbon-carbon double bonds, only one of the plurality of carbon-carbon double bonds can be selectively epoxidated in the case the environments of the double bonds are different. In particular, in the case of having a cyclohexene backbone and a terminal vinyl or vinylidene group in a molecule thereof, the double bond of the cyclohexene backbone can be selectively epoxidated.

An example of a substrate that is epoxidated in the process as claimed in the present invention is a compound represented by the following formula (7):

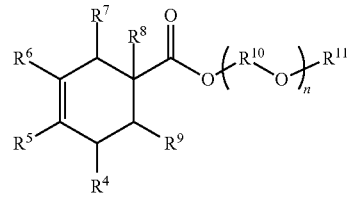

(wherein $R^4$, $R^5$, $R^6$, $R^7$ and $R^8$ each independently of the other represent a hydrogen atom or methyl group, $R^9$ represents a hydrogen atom, methyl group, phenyl group or the following $R^{12}$:

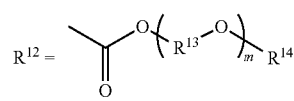

(wherein $R^{13}$ represents an $C_2$-$C_8$ alkylene or $C_2$-$C_8$ cycloalkylene group, $R^{14}$ represents an $C_1$-$C_{10}$ alkyl group, $C_1$-$C_{10}$ aryl group or $C_1$-$C_{10}$ alkenyl group, and m represents an integer of 0 to 5), $R^{10}$ represents an $C_2$-$C_8$ alkylene or $C_2$-$C_8$ cycloalkylene group, $R^{11}$ represents an $C_1$-$C_{10}$ alkyl group, $C_1$-$C_{10}$ cycloalkyl group, $C_1$-$C_{10}$ aryl group, $C_1$-$C_{10}$ alkenyl group or $C_1$-$C_{10}$ cycloalkenyl group, and n represents an integer of 0 to 5).

Similarly, an example of a substrate that is epoxidated in the process as claimed in the present invention is also a compound represented by the following formula (9):

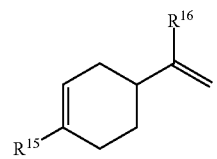

(wherein $R^{15}$ and $R^{16}$ represent hydrogen atoms or methyl groups).

Similarly, an example of a substrate that is epoxidated in the process as claimed in the present invention is also a compound represented by the following formula (10):

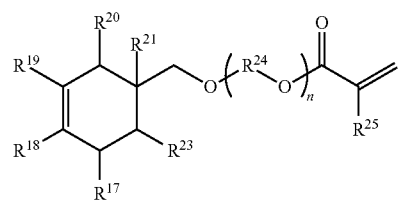

(wherein $R^{17}$, $R^{18}$, $R^{19}$, $R^{20}$, $R^{21}$, and $R^{25}$ each independently of the other represent a hydrogen atom or methyl group, $R^{23}$ represents a hydrogen atom, methyl group or phenyl group, $R^{24}$ represents an $C_2$-$C_8$ alkylene or $C_2$-$C_8$ cycloalkylene group, and n represents an integer of 0 to 5).

These substrates enable the epoxidation to proceed simply by mixing these substrates with an aqueous hydrogen peroxide solution and a catalyst without using a solvent (solvent-free).

In addition, in consideration of carrying out industrially stable production, the method used to carry out epoxidation preferably consists of first charging the catalyst and substrate into a reaction vessel, and gradually adding hydrogen peroxide while maintaining the reaction temperature at as constant a temperature as possible and while confirming consumption of hydrogen peroxide in the reaction. The use of such a method makes it possible to reduce the amount of hydrogen peroxide that accumulates and minimize any increases in pressure even if oxygen gas is generated within the reaction vessel due to abnormal decomposition of hydrogen peroxide.

Since an excessively high reaction temperature increases the number of side reactions, while an excessively low reaction temperature reduces the rate at which hydrogen peroxide is consumed thereby causing hydrogen peroxide to accumulate in the reaction system, the reaction temperature is preferably selected within a range of −10 to 120° C. and more preferably 10 to 90° C.

Examples of compounds represented by the aforementioned formula (7) include methyl 3-cyclohexene-1-carboxylate, ethyl 3-cyclohexene-1-carboxylate, phenyl 3-cyclohexene-1-carboxylate, benzyl 3-cyclohexene-1-carboxylate, cyclohexyl 3-cyclohexene-1-carboxylate, allyl 3-cyclohexene-1-carboxylate, 2'-alloxyethyl 3-cyclohexene-1-carboxylate, 2'-methyl-2'-propenyl 3-cyclohexene-1-carboxylate, 1'-methyl-2'-propenyl 3-cyclohexene-1-carboxylate, 1'-ethyl-2'-propenyl 3-cyclohexene-1-carboxylate, 1'-phenyl-2'-propenyl 3-cyclohexene-1-carboxylate, methyl 1-methyl-3-cyclohexene-1-carboxylate, ethyl 1-methyl-3-cyclohexene-1-carboxylate, phenyl 1-methyl-3-cyclohexene-1-carboxylate, benzyl 1-methyl-3-cyclohexene-1-carboxylate, cyclohexyl 1-methyl-3-cyclohexene-1-carboxylate, allyl 1-methyl-3-cyclohexene-1-carboxylate, 2'-allyloxyethyl 1-methyl-3-cyclohexene-1-carboxylate, methyl 3-cyclohexene-6-phenyl-1-carboxylate, ethyl 3-cyclohexene-6-phenyl-1-carboxylate, phenyl 3-cyclohexene-6-phenyl-1-carboxylate, benzyl 3-cyclohexene-6-phenyl-1-carboxylate, allyl 3-cyclohexene-6-phenyl-1-carboxylate, methyl 3-cyclohexene-3-methyl-1-carboxylate, ethyl 3-cyclohexene-3-methyl-1-carboxylate, phenyl 3-cyclohexene-3-methyl-1-carboxylate, benzyl 3-cyclohexene-3-methyl-1-carboxylate, allyl 3-cyclohexene-3-methyl-1-carboxylate, methyl 3-cyclohexene-4-methyl-1-carboxylate, ethyl 3-cyclohexene-4-methyl-1-carboxylate, phenyl 3-cyclohexene-4-methyl-1-carboxylate, benzyl 3-cyclohexene-4-methyl-1-carboxylate, allyl 3-cyclohexene-4-methyl-1-carboxylate, dimethyl 3-cyclohexene-1,6-dicarboxylate, diethyl 3-cyclohexene-1,6-dicarboxylate, diphenyl 3-cyclohexene-1,6-dicarboxylate, dibenzyl 3-cyclobexene-1,6-dicarboxylate, diallyl 3-cyclohexene-1,6-dicarboxylate, and 3-cyclohexenyl 3-cyclohexene-1-carboxylate.

In addition, examples of a compound represented by the aforementioned formula (9) include vinylcyclohexene and limonene, while examples of a compound represented by the aforementioned formula (10) include 3-cyclohexenylmethyl (meth)acrylate and 2-(3-cyclohexenylmethoxy)ethyl (meth)acrylate.

Among compounds represented by the aforementioned formulas (7) and (9), a compound represented by the following formula:

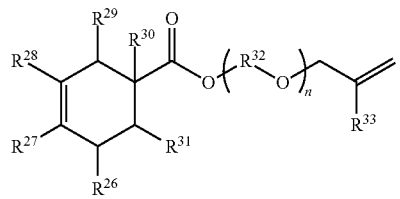

(wherein $R^{26}, R^{27}, R^{28}, R^{29}$ and $R^{30}$ each independently of the other represent a hydrogen atom or methyl group, $R^{31}$ represents a hydrogen atom, methyl group, phenyl group or the following $R^{34}$:

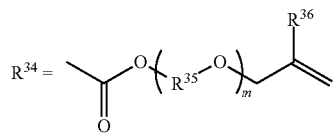

(wherein $R^{35}$ represents an $C_2$-$C_8$ alkylene or $C_2$-$C_8$ cycloalkylene group, $R^{36}$ represents a hydrogen atom or methyl group, and m represents an integer of 0 to 5), $R^{32}$ represents an $C_2$-$C_8$ alkylene or $C_2$-$C_8$ cycloalkylene group, $R^{33}$ represents a hydrogen atom or methyl group, and n represents an integer of 0 to 5), vinylcyclohexene, 3-cyclohexenylmethyl (meth)acrylate and limonene are particularly preferable since a double bond that can be used for denaturation is able to remain following epoxidation.

In addition, in the case of a compound represented by the aforementioned formula (9) in particular, since the reaction solution can be separated directly into an aqueous layer containing a tungsten compound and an organic layer containing the product and raw materials, the reaction solution can be supplied to the following purification step without particularly using an extraction solvent and the like following completion of the reaction by separating the reaction solution as is.

In the case of a compound represented by the aforementioned formula (7), although there may be cases in which there is hardly any difference between the specific gravities of the aqueous layer and organic layer, the two layers can be separated without having to use an organic extraction solvent in this case as well by mixing a saturated aqueous solution of an inorganic compound into the aqueous layer to make the specific gravity thereof different from that of the organic layer. Since the specific gravity of the tungsten compound is particularly high, in order to make the lower layer the aqueous layer, the tungsten compound may be used in an amount that exceeds the aforementioned amount used that is inherently required for use as a catalyst. In this case, the efficiency of the tungsten compound is preferably enhanced by reusing the tungsten compound obtained from the aqueous layer. In addition, since the specific gravity of the organic layer may conversely approach 1.2 depending on the substrate, in such cases, the aqueous layer can be made to be the upper layer and the organic layer can be made to be the lower layer by further adding water to cause the specific gravity of the aqueous layer to approach 1.

Furthermore, in the process as claimed in the present invention, extraction can be carried out using an organic solvent such as cyclohexane or hexane for the extraction solvent instead of the reaction solvent, and the optimum separation method can be selected corresponding to the circumstances.

After concentrating the organic layer separated from the aqueous layer in this manner, the resulting epoxy compound can be obtained by an ordinary method such as recrystallization, distillation or sublimation.

Although the following provides a more detailed explanation of the present invention using the following examples, the present invention is not limited to only these examples.

EXAMPLES

Example 1

0.360 g (1.84 mmol) of 50% aqueous sulfuric acid solution, 5.18 g (14.7 mmol) of trioctylamine (TNOA), 0.815 g (7.34 mmol) of aminomethylphosphonic acid, 4.61 g (14.7 mmol) of sodium tungstate dihydrate, 100 g (0.734 mol) of limonene and 3.57 g (36.7 mmol) of a 35% aqueous hydrogen peroxide solution were placed in a 300 mL three-necked, round-bottom flask equipped with a dropping funnel and Dimroth condenser, the temperature of the reaction solution was adjusted to 55° C., and 67.8 g (0.697 mol) of a 35% aqueous hydrogen peroxide solution were further dropped in while stirring over the course of 4 to 5 hours so that the reaction temperature did not exceed 60° C. Following completion of dropping, stirring was continued for 1 hour and the reaction solution was allowed to cool to room temperature. The reaction solution rapidly separated into two layers when stirring was discontinued, with the upper layer as the organic layer and the lower layer as the aqueous layer. As a result of analyzing the organic layer of the upper layer, the limonene conversion rate was 73% and the selectivity of limonene monooxide was 80%.

Furthermore, conversion rate and selectivity were calculated according to the following calculation formulas based on analysis results obtained by gas chromatography.

Conversion rate(%)=(1−no. of moles of raw materials remaining/no. of moles of raw materials used)×100

Selectivity(%)=(no. of moles of target compound/no. of moles of raw material used)×10000/conversion rate(%)

Example 2

0.391 g (2.0 mmol) of a 50% aqueous sulfuric acid solution, 0.707 g (2.0 mmol) of trioctylamine, 50 g (0.20 mol) of diallyl tetrahydrophthalate (DATHP), 1.320 g (4.0 mmol) of sodium tungstate dihydrate, 0.222 g (2.0 mmol) of aminomethylphosphonic acid and 0.969 g (9.97 mmol) of a 35% aqueous hydrogen peroxide solution were placed in a 300 mL three-necked flask equipped with a dropping funnel and Dimroth condenser, and after heating to 60° C. with an oil bath while stirring with a magnetic stirrer, 20.38 g (0.210 mol) of a 35% aqueous hydrogen peroxide solution were dropped in so that the reaction temperature did not exceed 65° C. Following completion of dropping, stirring was continued for 1 hour and the reaction solution was allowed to cool to room temperature. Subsequently, 100 g of pure water were added and the organic layer was separated with the upper layer as the aqueous layer and the lower layer as the organic layer. As a result of analyzing the organic layer, the conversion rate of diallyl tetrahydrophthalate was 95% and the selectivity of diallyl 4,5-epoxycyclohexane-1,2-dicarboxylate was 93%.

Example 3

1.44 g (7.34 mmol) of 50% aqueous sulfuric acid solution, 5.18 g (14.7 mmol) of trioctylamine (TNOA), 0.815 g (7.34 mmol) of aminomethylphosphonic acid, 4.61 g (14.7 mmol) of sodium tungstate dihydrate, 122 g (0.734 mol) of allyl 3-cyclohexene carboxylate and 3.57 g (36.7 mmol) of a 35% aqueous hydrogen peroxide solution were placed in a 300 mL three-necked, round-bottom flask equipped with a dropping funnel and Dimroth condenser, the temperature of the reaction solution was adjusted to 55° C., and 67.8 g (0.697 mol) of a 35% aqueous hydrogen peroxide solution were further dropped in while stirring over the course of 4 to 5 hours so that the reaction temperature did not exceed 60° C. Following completion of dropping, stirring was continued for 1 hour and the reaction solution was allowed to cool to room temperature. Following completion of the reaction, 50 g of hexane were dropped in to separate into two layers with the upper layer as the organic layer and the lower layer as the aqueous layer. As a result of analyzing the organic layer of the upper layer, the conversion rate of allyl 3-cyclohexene carboxylate was 87%, and the selectivity of allyl 3,4-epoxycyclohexane carboxylate was 93%.

Example 4

0.439 g (2.24 mmol) of 50% aqueous sulfuric acid solution, 3.17 g (14.7 mmol) of trioctylamine (TNOA), 31.4 g (0.224 mol) of methyl 3-cyclohexene-1-carboxylate, 1.48 g (4.48 mmol) of sodium tungstate dihydrate and 0.249 g (2.24 mmol) of aminomethylphosphonic acid were placed in a 300 mL three-necked flask equipped with a dropping funnel and Dimroth condenser, and after heating to 60° C. with an oil bath while stirring with a magnetic stirrer, 47.9 g (0.492 mol) of a 35% aqueous hydrogen peroxide solution were dropped in so that the reaction temperature did not exceed 65° C. Following completion of dropping, stirring was continued for 1 hour and the reaction solution was allowed to cool to room temperature. Subsequently, 50 g of ethyl acetate were added and the organic layer was separated with the upper layer as the organic layer and the lower layer as the aqueous layer. As a result of analyzing the organic layer, the conversion rate of methyl 3-cyclohexene-1-carboxylate was 95%, and the selectivity of methyl 3,4-epoxycyclohexane carboxylate was 82%.

Example 5

0.439 g (2.24 mmol) of 50% aqueous sulfuric acid solution, 3.29 g (8.95 mmol) of Amine M-210D (N-methyldidecylamine, Lion Akzo Co., Ltd.), 50 g (0.224 mol) of 3-cyclohexenyl 3-cyclohexene-1-carboxylate, 1.48 g (4.48 mmol) of sodium tungstate dihydrate and 0.249 g (2.24 mmol) of aminomethylphosphonic acid were placed in a 300 mL three-necked flask equipped with a dropping funnel and Dimroth condenser, and after heating to 60° C. with an oil bath while stirring with a magnetic stirrer, 47.9 g (0.492 mol) of a 35% aqueous hydrogen peroxide solution were dropped in so that the reaction temperature did not exceed 65° C. Following completion of dropping, stirring was continued for 1 hour and the reaction solution was allowed to cool to room temperature. Subsequently, 50 g of ethyl acetate were added and the organic layer was separated with the upper layer as the organic layer and the lower layer as the aqueous layer. As a result of analyzing the organic layer, the conversion rate of 3-cyclohexenyl 3-cyclohexene-1-carboxylate was 96%, the selectivity of 3,4-epoxycyclohexylmethyl 3',4'-epoxycyclohexane carboxylate was 51%, and 27% of a monoepoxy form of the intermediate was also formed.

Example 6

0.268 g (1.37 mmol) of 50% aqueous sulfuric acid solution, 0.483 g (1.37 mmol) of trioctylamine, 50 g (0.273 mol) of 3-cyclohexenylmethyl methacrylate, 0.902 g (2.73 mmol) of sodium tungstate dihydrate and 0.152 g (1.37 mmol) of aminomethylphosphonic acid were placed in a 300 mL three-necked flask equipped with a dropping funnel and Dimroth condenser, and after heating to 50° C. with an oil bath while stirring with a magnetic stirrer, 23.9 g (0.246 mol) of a 35% aqueous hydrogen peroxide solution were dropped in so that the reaction temperature did not exceed 55° C. Following completion of dropping, stirring was continued for 1 hour and the reaction solution was allowed to cool to room temperature. Subsequently, 50 g of ethyl acetate were added and the organic layer was separated with the upper layer as the organic layer and the lower layer as the aqueous layer. As a result of analyzing the organic layer, the conversion rate of 3-cyclohexenylmethyl methacrylate was 52%, and the selectivity of 3,4-epoxycyclohexylmethyl methacrylate was 98%.

Example 7

20.0 g (60.6 mmol) of sodium tungstate, 5.95 g (30.3 mmol) of a 50% aqueous sulfuric acid solution, 34 g of pure water and 5.90 g (60.7 mmol) of a 35% aqueous hydrogen peroxide solution were dissolved in advance.

25.7 g of the previously prepared aqueous tungstic acid solution, 4.26 g (12.0 mmol) of trioctylamine (TNOA), 1.34 g (12.0 mmol) of 88% phosphoric acid and 400 g (2.41 mol) of allyl 3-cyclohexene carboxylate were placed in a 2000 mL three-necked flask equipped with a dropping funnel and Dimroth condenser, the reaction solution was adjusted to a temperature of 70° C., and 210 g (2.17 mol) of a 35% aqueous hydrogen peroxide solution were further dropped in while stirring over the course of 8 hours so that the reaction temperature did not exceed 75° C. Following completion of dropping, stirring was continued for 1 hour and the reaction solution was allowed to cool to room temperature. Following completion of the reaction, 400 g of ethyl acetate were added to separate into two layers with the upper layer as the organic layer and the lower layer as the aqueous layer. As a result of analyzing the organic layer of the upper layer, the conversion rate of allyl 3-cyclohexene carboxylate was 83%, and the selectivity of allyl 3,4-epoxycyclohexane carboxylate was 91%.

The organic layer of the upper layer was then washed twice with 50 g of saturated aqueous sodium thiosulfate solution (total amount used: 100 g), and after further washing with 50 g of pure water, the ethyl acetate was distilled off with an evaporator and 64 g of raw material in the form of allyl 3-cyclohexene carboxylate and 282 g of product in the form of allyl 3,4-epoxycyclohexane carboxylate were recovered. Although the residue was viscous, it had not gelled, and as a result of extracting with hexane and analyzing by gas chromatography, the extract was confirmed to contain 28 g of the product in the form of allyl 3,4-epoxycyclohexane carboxylate.

Comparative Example 1

20.0 g (60.6 mmol) of sodium tungstate, 5.95 g (30.3 mmol) of a 50% aqueous sulfuric acid solution, 34 g of pure water and 5.90 g (60.7 mmol) of a 35% aqueous hydrogen peroxide solution were dissolved in advance.

25.7 g of the previously prepared aqueous tungstic acid solution, 4.86 g (12.0 mmol) of trioctylmethyl ammonium chloride, 1.34 g (12.0 mmol) of aminomethylphosphonic acid and 400 g (2.41 mol) of allyl 3-cyclohexene carboxylate were placed in a 2000 mL three-necked flask equipped with a dropping funnel and Dimroth condenser, the reaction solution was adjusted to a temperature of 70° C., and 210 g (2.17 mol) of a 35% aqueous hydrogen peroxide solution were further dropped in while stirring over the course of 8 hours so that the reaction temperature did not exceed 75° C. Following completion of dropping, stirring was continued for 1 hour and the reaction solution was allowed to cool to room temperature. Following completion of the reaction, 400 g of ethyl acetate were added to separate into two layers with the upper layer as the organic layer and the lower layer as the aqueous layer. As a result of analyzing the organic layer of the upper layer, the conversion rate of allyl 3-cyclohexene carboxylate was 80%, and the selectivity of allyl 3,4-epoxycyclohexane carboxylate was 98%.

The organic layer of the upper layer was then washed twice with 50 g of saturated aqueous sodium thiosulfate solution (total amount used: 100 g), and after further washing with 50 g of pure water, the ethyl acetate was distilled off with an evaporator and although vacuum distillation was carried out, only 66 g of raw material in the form of allyl 3-cyclohexene carboxylate and 168 g of product in the form of allyl 3,4-epoxycyclohexane carboxylate were able to be recovered. In addition, the residue had gelled and prevented recovery of the product therefrom.

INDUSTRIAL APPLICABILITY

The present invention provides a novel and efficient process for producing a polyfunctional epoxy monomer that facilitates separation of an aqueous layer catalyst from the reaction solution by reacting a compound having a plurality of carbon-carbon double bonds in a molecule thereof with an aqueous hydrogen peroxide solution by using a tungsten compound and a tertiary organic amine as catalysts under mild conditions without using an organic solvent or strong phase transfer catalyst in the manner of a quaternary ammonium salt. Namely, the present invention allows the selective production of a bifunctional epoxy monomer from a diolefin at satisfactory yield and low cost while using a simple and safe procedure under mild conditions without using an organic solvent. Organic polyfunctional epoxy monomers are useful compounds that can be widely used in various industrial fields including the chemical industry as raw materials of resist materials (and particularly solder resist materials), and as intermediates of agricultural chemicals and pharmaceuticals as well as raw materials of various polymers such as plasticizers, adhesives or coating resins.

The invention claimed is:
1. A process for producing an epoxy compound comprising the step of:
  producing a corresponding epoxy compound by reacting an organic compound having a carbon-carbon double bond with hydrogen peroxide present in an aqueous hydrogen peroxide solution to epoxidize the double bond;
  wherein an organic solvent is not used as a reaction solvent, and a tungsten compound and tertiary amine are used as reaction catalysts, wherein the compound having a carbon-carbon double bond has a plurality of carbon-carbon double bonds, and only one of the plurality of carbon-carbon double bonds is selectively epoxidized, and wherein the organic compound having a plurality of carbon-carbon double bonds is a compound having a cyclohexene backbone and a terminal vinyl or vinylidene group in a molecule thereof, and the carbon-carbon double bond moiety of the cyclohexene backbone is epoxidized, wherein an α-aminomethylphosphonic acid compound represented by the following structural formula:

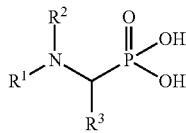

wherein $R^1$ represents a hydrogen atom or acyl group, and $R^2$ and $R^3$ each independently of the other represent a hydrogen atom or $C_1$-$C_{18}$ alkyl group or $C_1$-$C_{18}$ aryl, is further used as a co-catalyst.

2. The process for producing an epoxy compound according to claim 1, wherein a mineral acid and/or partially neutralized salt thereof is further used as a co-catalyst.

3. The process for producing an epoxy compound according to claim 1, wherein the organic compound having a plurality of carbon-carbon double bonds is a compound represented by the following formula:

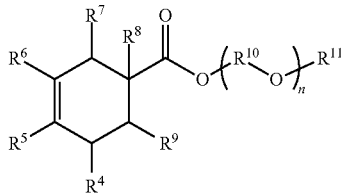

wherein $R^4$, $R^5$, $R^6$, $R^7$ and $R^8$ each independently of the other represent a hydrogen atom or methyl group, $R^9$ represents a hydrogen atom, methyl group, phenyl group or the following $R^{12}$:

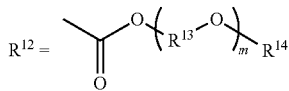

wherein $R^{13}$ represents a $C_2$-$C_8$ alkylene or $C_2$-$C_8$ cycloalkylene group, $R^{14}$ represents a $C_1$-$C_{10}$ alkyl group, $C_1$-$C_{10}$ cycloalkyl group, $C_1$-$C_{10}$ aryl group, $C_1$-$C_{10}$ alkenyl group having a terminal vinyl or vinylidene group or $C_1$-$C_{10}$ cycloalkenyl group, and m represents an integer of 0 to 5, $R^{10}$ represents a $C_2$-$C_8$ alkylene or $C_2$-$C_8$ cycloalkylene group, $R^{11}$ represents a $C_1$-$C_{10}$ alkyl group, $C_1$-$C_{10}$ cycloalkyl group, $C_1$-$C_{10}$ aryl group, $C_1$-$C_{10}$ alkenyl group having a terminal vinyl or vinylidene group or $C_1$-$C_{10}$ cycloalkenyl group, provided that at least one of $R^{11}$ and $R^{14}$ is a $C_1$-$C_{10}$ alkenyl group having a terminal vinyl or vinylidene group, and n represents an integer of 0 to 5.

4. The process for producing an epoxy compound according to claim 1, wherein the organic compound having a plurality of carbon-carbon double bonds is a compound represented by the following formula:

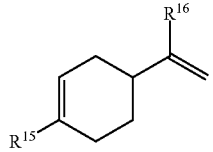

wherein $R^{15}$ and $R^{16}$ represent hydrogen atoms or methyl groups.

5. The process for producing an epoxy compound according to claim 1, wherein the organic compound having a plurality of carbon-carbon double bonds is a compound represented by the following formula:

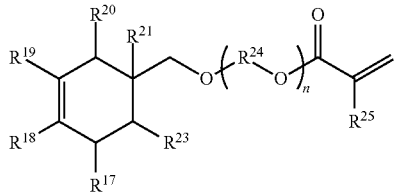

wherein $R^{17}$, $R^{18}$, $R^{19}$, $R^{20}$, $R^{21}$, and $R^{25}$ each independently of the other represent a hydrogen atom or methyl group, $R^{23}$ represents a hydrogen atom, methyl group or phenyl group, $R^{24}$ represents a $C_2$-$C_8$ alkylene or $C_2$-$C_8$ cycloalkylene group, and n represents an integer of 0 to 5.

6. The process for producing an epoxy compound according to claim 1, wherein the tungsten compound is sodium tungstate, and the tertiary amine is a tertiary amine having an alkyl group in which the total number of carbon atoms is 6 or more.

7. The process for producing an epoxy compound according to claim 2, wherein the mineral acid and/or partially neutralized salt thereof is at least one type selected from the group consisting of phosphoric acid, sulfuric acid and boric acid and/or partially neutralized salts thereof.

8. The process for producing an epoxy compound according to claim 1, wherein the total number of carbon atoms of an alkyl group of the tertiary amine is 12 to 40.

9. The process for producing an epoxy compound according to claim 1, wherein the organic compound having a plurality of carbon-carbon double bonds is 3-cyclohexenylmethyl (meth)acrylate and/or allyl 3-cyclohexene-1-carboxylate.

* * * * *